(12) United States Patent
Niunoya et al.

(10) Patent No.: US 9,580,217 B2
(45) Date of Patent: Feb. 28, 2017

(54) PLUG

(75) Inventors: Masatoshi Niunoya, Shunan (JP);
Ryusuke Okamoto, Shunan (JP)

(73) Assignee: SEKISUI MEDICAL CO., LTD.,
Tokyo (JP)

( * ) Notice: Subject to any disclaimer, the term of this patent is extended or adjusted under 35 U.S.C. 154(b) by 0 days.

(21) Appl. No.: 13/816,221

(22) PCT Filed: Aug. 16, 2011

(86) PCT No.: PCT/JP2011/068550
§ 371 (c)(1),
(2), (4) Date: Feb. 8, 2013

(87) PCT Pub. No.: WO2012/023554
PCT Pub. Date: Feb. 23, 2012

(65) Prior Publication Data
US 2013/0134122 A1    May 30, 2013

(30) Foreign Application Priority Data

Aug. 20, 2010 (JP) .................... 2010-185375

(51) Int. Cl.
*A61B 5/15*    (2006.01)
*B65D 51/18*   (2006.01)
(Continued)

(52) U.S. Cl.
CPC .......... *B65D 51/18* (2013.01); *A61B 5/15003* (2013.01); *A61B 5/154* (2013.01);
(Continued)

(58) Field of Classification Search
CPC .......... B65D 51/002; B65D 51/18; A61J 1/10; A61J 1/1406; A61B 5/15003; A61B 5/154;
(Continued)

(56) References Cited

U.S. PATENT DOCUMENTS 4,465,200 A * 8/1984 Percarpio ..................... 215/247
4,967,919 A * 11/1990 Earhart ......................... 215/247
(Continued)

FOREIGN PATENT DOCUMENTS

CN    1628599 A    6/2005
CN    101721217 A  6/2010
(Continued)

OTHER PUBLICATIONS

Written Opinion of the International Searching Authority (PCT/ISA/237) for Application No. PCT/JP2011/068550 mailed Mar. 28, 2013.
(Continued)

*Primary Examiner* — James N Smalley
(74) *Attorney, Agent, or Firm* — Cheng Law Group, PLLC

(57) ABSTRACT

Provided is a plug that enables reliable and easy removal of a plug body together with a cover member from a tubular container without increasing an outwardly-bulging flange portion of a grip part of the plug body and is superior in productivity. A plug 1 for closing an open end of an open-ended tubular container 4. A cover member 3 is fitted on a plug body 2 including a press-fit part 2a and a grip part 2b. An engagement portion 3d is extended from a head plate 3a of the cover member 3 into a recess 2d in the upper surface of the plug body 2 to face an inside wall 2e surrounding the recess 2d. When an external force is applied to incline the head plate 3a with respect to the upper surface of the plug body 2, the engagement portion 3d is engaged to the inside wall 2e.

8 Claims, 9 Drawing Sheets

(51) Int. Cl.
*A61J 1/14* (2006.01)
*A61B 5/154* (2006.01)

(52) U.S. Cl.
CPC ....... *A61B 5/150351* (2013.01); *A61J 1/1406* (2013.01); *B01L 2300/042* (2013.01)

(58) Field of Classification Search
CPC ............ A61B 5/150351; A61B 5/1438; B01L 2300/042
USPC ................................. 215/247, 249; 604/415
See application file for complete search history.

(56) References Cited

U.S. PATENT DOCUMENTS

| | | | |
|---|---|---|---|
| 5,232,111 A | | 8/1993 | Burns |
| 5,294,011 A | | 3/1994 | Konrad et al. |
| 5,361,921 A | | 11/1994 | Burns |
| 5,699,923 A | * | 12/1997 | Burns .......................... 215/247 |
| 2006/0235356 A1 | | 10/2006 | Yamaya |

FOREIGN PATENT DOCUMENTS

| | | |
|---|---|---|
| CN | 201551571 U | 8/2010 |
| EP | 0 623 523 A1 | 11/1994 |
| EP | 0 634 339 A1 | 1/1995 |
| JP | 6-194280 A | 7/1994 |
| JP | 7-51254 A | 2/1995 |
| JP | 3064444 B2 | 7/2000 |
| JP | 4198309 B2 | 12/2008 |

OTHER PUBLICATIONS

International Search Report for the Application No. PCT/JP2011/068550 mailed Sep. 27, 2011.
The First Office Action for Application No. 201180040290.7 from The State Intellectual Property Office of the People's Republic of China dated Sep. 30, 2014.
Supplementary European Search Report for the Application No. EP 11 81 8195 dated Feb. 13, 2015.

* cited by examiner (a)

(b)

(c)

(a)

(b)

(a)

(b)

(a)

(b)

(a)

(b)

(c)

PLUG

TECHNICAL FIELD

This invention relates to a plug for closing open end of an open-ended tubular container, such as a blood collection tube, and particularly relates to a plug in which a cover member is fitted on a plug body made of rubber or the like.

BACKGROUND ART

Plugs made of rubber, elastomer or the like are conventionally used in order to seal bodily fluid collection tubes, such as a vacuum blood collection tube.

Patent Literature 1 below discloses an example of a plug of this kind. FIG. 9(a) is a partly cutaway front cross-sectional view for illustrating a plug described in Patent Literature 1. The plug 102 is attached to an upper end opening of a closed-bottomed, cylindrical, bodily fluid collection tube 101 to seal it. The plug 102 includes a plug body 103 made of rubber, elastomer or the like and a cover member 104. The plug body 103 includes a press-fit part 103a press-fitted into the bodily fluid collection tube 101; and a grip part 103b continued upward from the press-fit part 103a. The cover member 104 is fitted to the grip part 103b to cover the grip part 103b.

The cover member 104 includes a head plate 104a engaging against the upper surface of the grip part 103b of the plug body 103. A skirt 104b is provided to extend downward from the outer peripheral edge of the head plate 104a.

Alternatively, Patent Literature 2 below discloses a plug 111 shown in front cross-section in FIG. 10. The plug 111 includes a plug body 112 made of rubber, elastomer or the like and a cover member 113 fitted on the plug body 112. A press-fit part 112a of the plug body 112 is press-fitted into a bodily fluid collection tube 101. A grip part 112b continued upward from the press-fit part 112a is covered by the cover member 113.

An annular retaining ring 114 is placed on the upper surface of the grip part 112b. The cover member 113 has a tubular shape. An annular extension 113a is provided to extend inward from the upper open edge of the cover member 113. The retaining ring 114 is engaged to the annular extension 113a against slipping out upward.

The cover member 113 is provided at the middle of the height with an annular engagement ledge 113b extending inward from the inside wall of the cover member 113. The annular engagement ledge 113b is clamped between the lower surface of the grip part 112b of the plug body 112 and the upper end of the bodily fluid collection tube 101. Specifically, the grip part 112b is formed to have a larger diameter than the press-fit part 112a of the plug body 112, so that a shoulder 112c is formed on the lower surface of the grip part 112b. The annular engagement ledge 113b is engaged against this shoulder 112c.

The cover members 104, 113 described in Patent Literatures 1 and 2 are provided to allow examining staffs to easily remove the plug bodies 103, 112 from the bodily fluid collection tubes 101 without touching the plug bodies 103, 112 with their hands. Specifically, by applying a force to the cover members 104, 113 with fingers to move it away upward from the bodily fluid collection tubes 101, the plug bodies 103, 112 can be removed together with the cover members 104, 113 from the bodily fluid collection tubes 101.

CITATION LIST

Patent Literature

Patent Literature 1: JP-B-4198309
Patent Literature 2: JP-B-3064444

SUMMARY OF INVENTION

Technical Problem

However, the plug 102 having such a configuration as described in Patent Literature 1 may cause a failure of removal of the plug body 103 together with the cover member 104. Specifically, in removing the plug body 103, as shown by the arrow in FIG. 9(b), an external force is applied obliquely upward to the cover member 104 while the cover member 104 is twisted relative to the bodily fluid collection tube. When it is attempted to remove the plug body 103 from the bodily fluid collection tube 101 in the above manner, only the cover member 104 may be removed to leave the plug body 103 press-fitted in the bodily fluid collection tube 101. Therefore, the examining staff or the like may have to remove the plug body 103 from the bodily fluid collection tube 101 with his/her fingers. Thus, the cover member 104 for preventing contagion may not be able to perform its intended function.

In order to solve the above problem, for example, it is conceivable to increase the area of a shoulder 103c located at the lower surface of the grip part 103b in FIG. 9(a). In this case, however, the shoulder 103c upward of the press-fit part 103a must be increased in outside diameter. In other words, the volume of a flange portion of the grip part 103b bulging outward beyond the press-fit part 103a (and thus the grip part volume) must be increased. This presents a problem of increased volume of the plug body 103, resulting in increased medical waste.

On the other hand, in the plug 111 having such a configuration as described in Patent Literature 2, the annular engagement ledge 113b is engaged against the annular shoulder 112c of the plug body 112. Therefore, even when an external force is applied obliquely upward to the cover member 113 while the cover member 113 is twisted relative to the bodily fluid collection tube 101, the annular engagement ledge 113b is held engaged state against the shoulder 112c. As a result, the plug body 112 can be reliably removed together with the cover member 113 from the bodily fluid collection tube 101.

However, the plug 111 is composed of three members: the plug body 112, the cover member 113, and the retaining ring 114. Therefore, there arises a problem in that the number of elements is large, which makes the assembly process complicated. In addition, during assembly, the annular extension 113a for engaging the retaining ring 114 may be broken so that the retaining ring 114 may slip out. This presents another problem of low productivity.

An object of the present invention is to provide a plug that can eliminate the above disadvantages of the conventional techniques, enables easy and reliable removal of a plug body together with a cover member from an open end of a tubular container without increasing the volume of the above-mentioned flange portion of the plug body, i.e., the grip part volume, has a small number of elements, can be easily assembled, and is superior in productivity.

Solution to Problem

The present invention is a plug for closing an open end of an open-ended tubular container. The plug of the present invention includes a plug body and a cover member. The plug body includes: a press-fit part to be press-fitted into the open end of the tubular container; and a grip part continuous with the top of the press-fit part and having a larger diameter than the press-fit part, wherein an upper surface of the grip part has a recess formed therein and surrounded by an inside wall extending downward. The cover member includes a head plate and a skirt extending downward from a peripheral edge of the head plate and is fitted on the plug body so that a lower surface of the head plate and the upper surface of the grip part of the plug body face each other.

In the plug according to the present invention, an engagement portion provided at the head plate of the cover member and engaged to the inside wall surrounding the recess of the entire plug is extended from the head plate of the cover member to the interior of the recess to face a surface of the inside wall surrounding the recess of the plug body.

In a particular aspect of the plug according to the present invention, the engagement portion is engaged against the inside wall surrounding the recess of the plug body. In this case, since the engagement portion of the cover member is engaged against the inside wall of the plug body, an external force applied to the cover member is immediately applied also to the inside wall of the plug body. Therefore, the plug body can be more reliably removed together with the cover member.

In another particular aspect of the plug according to the present invention, at least a portion of an inside surface of the head plate of the cover member is engaged against the upper surface of the grip part of the plug body. In this case, since no gap exists between the inside surface of the head plate and the upper surface of the grip part, the dimension of the plug in the height direction can be reduced.

In still another particular aspect of the plug according to the present invention, the inside wall surrounding the recess of the plug body is an annular inside wall and the engagement portion includes a curved surface portion having a shape fitting the annular inside wall. In this case, even when an external force is applied obliquely upward to the cover member while the cover member is twisted relative to a bodily fluid collection tube, the force can be immediately applied through the engagement portion to the annular inside wall of the grip part. Thus, the plug body can be more reliably removed together with the cover member. Preferably, the engagement portion has a cylindrical shape. In this case, the plug body can be still more reliably removed together with the cover member.

In still another particular aspect of the plug according to the present invention, an outer peripheral edge of the grip part of the plug body is located below an outer peripheral edge of the recess in the grip part to thus create a space between the head plate of the cover member and the upper surface of the plug body, and the head plate of the cover member is provided at a portion thereof facing the space with a rib extending downward from the head plate and engaging against the upper surface of the grip part of the plug body. In this case, since the space is created between the head plate of the cover member and the upper surface of the plug body but the rib is provided, the plug body can be reliably removed together with the cover member from the tubular container.

In still another particular aspect of the plug according to the present invention, the upper surface of the grip part of the plug body is an inclined surface gradually lowering from the outer peripheral edge of the recess toward the outer peripheral edge of the grip part and the rib is provided to engage against the inclined surface. In this manner, by providing the rib so that also when the upper surface of the grip part is the inclined surface, the rib engages against the inclined surface, the plug body can be reliably removed together with the cover member from the tubular container.

Advantageous Effects of Invention

In the plug according to the present invention, since the cover member is provided with the engagement portion described above and the engagement portion is extended from the head plate of the cover member to the interior of the recess of the plug body to face the surface of the inside wall surrounding the recess, the engagement portion is engaged to the inside wall of the plug body when an external force is applied to incline the head plate of the cover member with respect to the upper surface of the plug body or an external force is applied obliquely upward while the cover member is twisted relative to a bodily fluid collection tube. Therefore, in removing the cover member, the plug body can be easily and reliably removed together with the cover member from the open end of the tubular container. Furthermore, without increasing the volume of the flange portion of the plug body, the plug body can be reliably removed together with the cover member from the tubular container in the above manner. Therefore, this can reduce the cost of the plug body and reduce medical waste. In addition, it suffices if the plug includes the plug body and the cover member, and there is no need for such a retaining ring as described in Patent Literature 2 and for any complicated structure for engaging the retaining ring. Therefore, the number of elements can be reduced and the assembly process can be simplified. Hence, a plug can be provided which is superior in productivity and inexpensive.

The present invention enables the examining staff or the like to reliably remove the plug body together with the cover member simply by applying an external force to the cover member without touching the plug body with his/her fingers. Therefore, the risks of contagion and the like of the examining staff can be reduced.

DESCRIPTION OF EMBODIMENTS

Hereinafter, the present invention will become apparent by explaining specific embodiments of the present invention with reference to the drawings.

Figure 1:
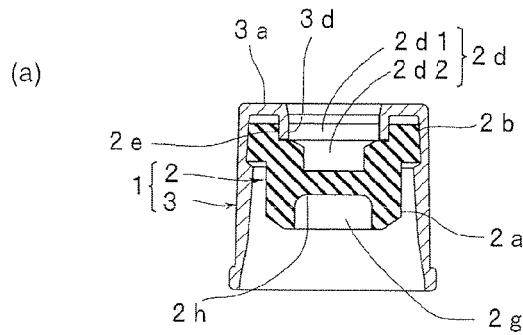
FIG. 1(*a*) is a front cross-sectional view of a plug according to a first embodiment of the present invention, FIG. 1(*b*) is a partly cutaway front cross-sectional view showing a state that the plug shown in FIG. 1(*a*) is attached to a tubular container, and FIG. 1(*c*) is a front cross-sectional view showing a modification of the plug.
Figure 1:
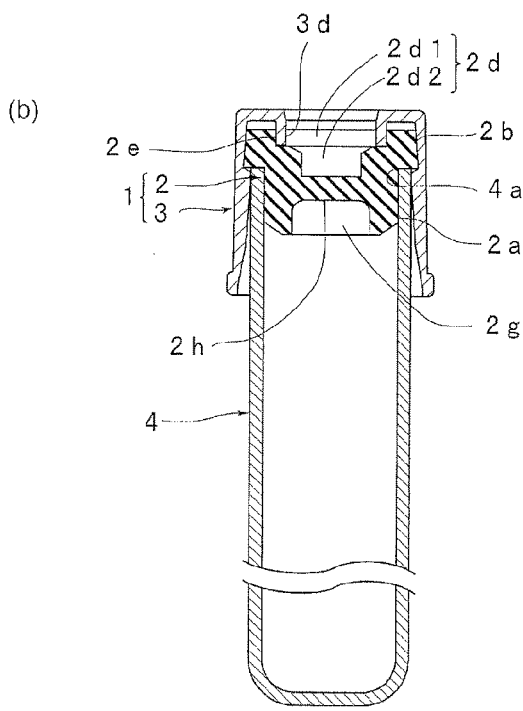
Figure 1:
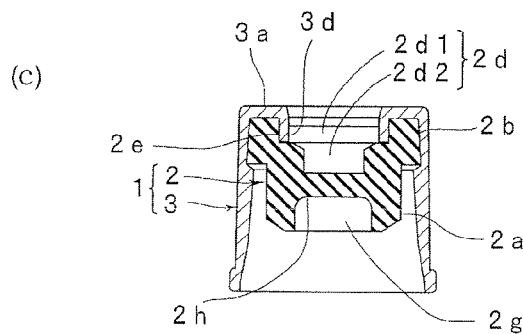

FIG. 1(a) is a front cross-sectional view showing a plug according to a first embodiment of the present invention and FIG. 1(b) is a partly cutaway front cross-sectional view showing a state that the plug is attached to a tubular container.

The plug 1 includes a plug body 2 and a cover member 3. Therefore, the plug 1 is composed of the two members.

As shown in FIG. 1(b), the plug 1 is attached to a tubular container 4 to seal an opening 4a located at the upper end of the tubular container 4. The tubular container 4 is a closed-bottomed, cylindrical container having an opening 4a at the upper end thereof. By attaching the plug 1 to the tubular container 4 under reduced pressure, a vacuum blood collection tube is constructed. However, the tubular container 4 may be any bodily fluid collection container for collecting various bodily fluids, not only the blood collection tube.

The plug body 2 is made of an elastic material, such as rubber or elastomer.

Figure 2:
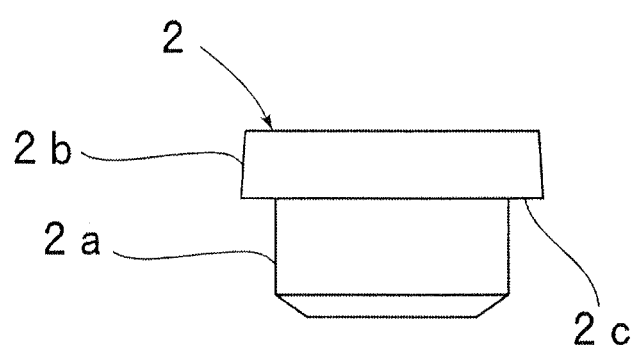
FIG. 2(*a*) is a front view of a plug body used in the first embodiment of the present invention and FIG. 2(*b*) is a front cross-sectional view thereof.
Figure 2:
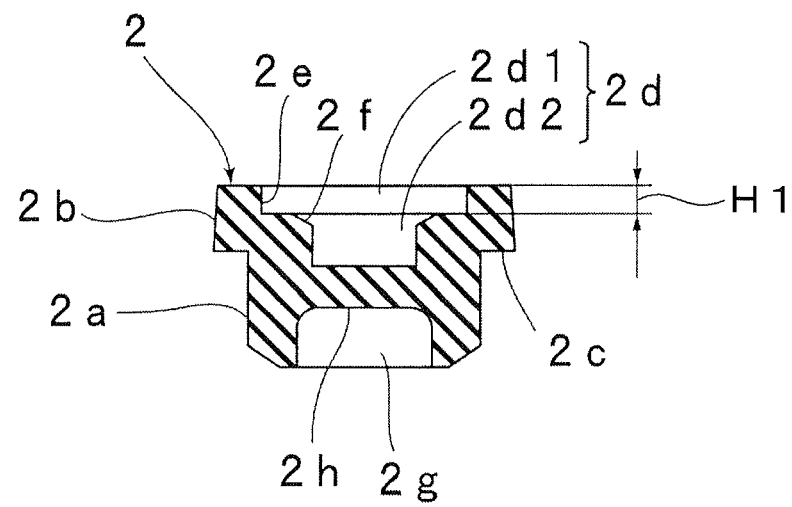

As shown in FIGS. 2(a) and 2(b), the plug body 2 includes a press-fit part 2a and a grip part 2b continued upward from the press-fit part 2a. The press-fit part 2a, as shown in FIG. 1(b), is a portion to be press-fitted into the interior of the tubular container 4. Since the tubular container 4 is cylindrically tubular, the press-fit part 2a has a cylindrical shape. However, the shape of the press-fit part 2a can be changed depending upon the shape of the tubular container 4.

The grip part 2b has a larger diameter than the press-fit part 2a. Since, therefore, the grip part 2b bulges outward beyond the press-fit part 2a, an annular shoulder 2c is formed on the lower surface of the grip part 2b.

As shown in FIG. 2(b), a recess 2d is formed to open into the upper surface of the grip part 2b, i.e., the upper surface of the plug body 2. The recess 2d is surrounded by a cylindrical inside wall 2e continuous with the upper surface of the grip part 2b. Note that in this embodiment the recess 2d is extended downward beyond the inside wall 2e. More specifically, a lower portion 2d2 of the recess 2d is provided which has a smaller diameter than an upper portion 2d1 thereof surrounded by the inside wall 2e. At the junction between the upper portion 2d1 and the lower portion 2d2, an annular inclined surface 2f is provided to gradually reduce the diameter downward.

On the other hand, the press-fit part 2a of the plug body 2 has a recess 2g formed to open into the lower surface thereof. Since the recess 2d and the recess 2g are formed, a thin-walled portion 2h is formed between the recess 2d and the recess 2g. The thin-walled portion 2h is a portion to be pierced through by a vacuum blood collection needle. Since the thickness of the thin-walled portion 2h is smaller than that of the plug body 2, the thin-walled portion 2h can be easily pierced through by a vacuum blood collection needle.

Although in this embodiment not only the upper portion 2d1 surrounded by the inside wall 2e but also the lower portion 2d2 are provided, the lower portion 2d2 may not be provided. In other words, the thin-walled portion 2h may be located just below the upper portion 2d1.

However, the lower portion 2d2 is preferably provided, which makes the thickness of the thin-walled portion 2h smaller. Thus, the resistance to piercing can be reduced.

The annular inside wall 2e has a cylindrical shape. Therefore, the annular inside wall 2e surrounds the recess 2d and extends in a vertical direction.

In this embodiment, the cover member 3 is formed of a synthetic resin molded article. However, the cover member 3 may be made of metal or other materials.

Figure 3:
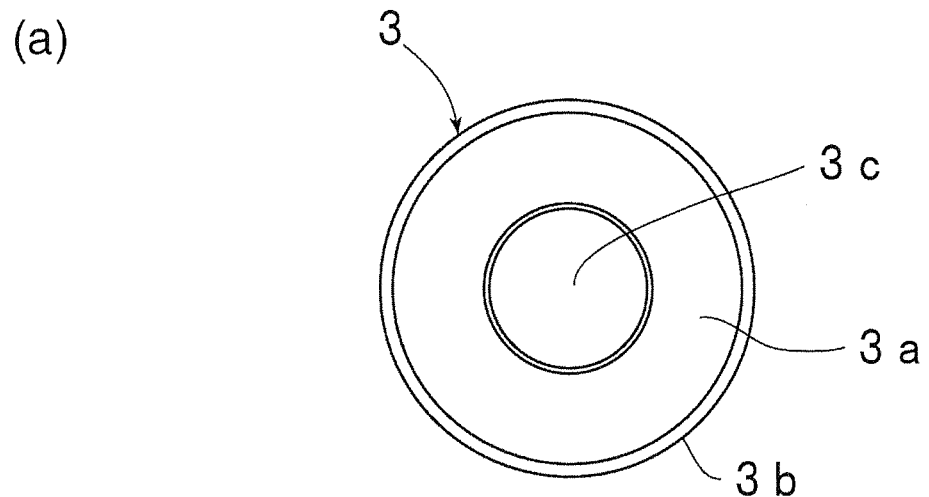
FIG. 3(*a*) is a plan view of a cover member used in the plug of the first embodiment of the present invention and FIG. 3(*b*) is a front cross-sectional view thereof.
Figure 3:
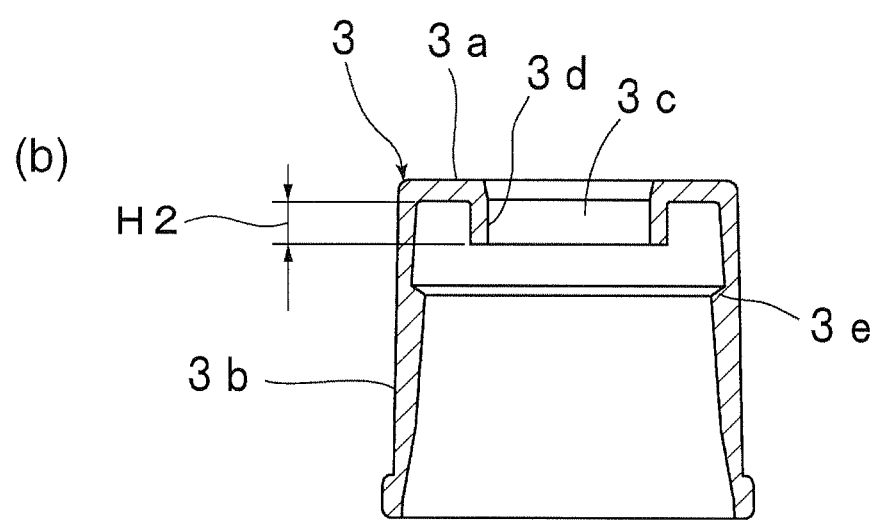

As shown in FIGS. 3(a) and 3(b), the cover member 3 includes a head plate 3a and a skirt 3b integrally provided with the head plate 3a to extend downward from an outer peripheral edge of the head plate 3a. In this embodiment, the outer peripheral edge of the head plate 3a has a circular shape. Therefore, the cover member 3 has an approximately cylindrical shape.

When attached to the tubular container 4, as shown in FIG. 1(b), the skirt 3b covers the plug body 2 and also covers an upper portion of the outside wall of the tubular container 4. The cover member 3 is provided in order to prevent the fingers of the examining staff from touching the opening 4a of the tubular container 4 and the plug body 2.

A circular opening 3c is formed in the center of the head plate 3a. An annular engagement portion 3d extending downward from the open edge of the opening 3c is provided continuously with the head plate 3a. In this embodiment, the engagement portion 3d has a cylindrical shape. However, the engagement portion 3d may be formed of a plurality of curved surface portions obtained by segmenting a cylindrical curved surface.

The engagement portion 3d extends in a vertical direction. Furthermore, an annular shoulder 3e is formed on the inner peripheral surface of the cover member 3. The inside diameter of a portion of the cover member 3 upward of the annular shoulder 3e is set at a diameter that allows the grip part 2b of the plug body 2 to be inserted thereinto. Specifically, the inside diameter of the portion of the cover member 3 upward of the annular shoulder 3e is equal to the outside diameter of the grip part 2b but may be slightly smaller than the outside diameter of the grip part 2b so long as the grip part 2b can be press-fitted into it. Alternatively, the inside diameter of the portion upward of the annular shoulder 3e may be larger than the outside diameter of the grip part 2b. In this case, when the cover member 3 is fitted on the plug body 2, a clearance will be created between the outer peripheral surface of the grip part 2b and the inner peripheral surface of the cover member 3, which may cause backlash. Preferably, it is desired that the inside diameter of the portion of the cover member 3 upward of the annular shoulder 3e be engaged against the outer peripheral surface of the grip part 2b to create no clearance therebetween.

When the cover member 3 is fitted on the plug body 2, the annular shoulder 3e engages the shoulder 2c located at the lower surface of the grip part 2b as shown in FIG. 1(a), which prevents the plug body 2 from slipping out downward.

As shown in FIG. 1(a), by inserting the plug body 2 into the cover member 3, in other words, by fitting the cover member 3 on the plug body 2, the cover member 3 can be locked to the plug body 2. In this state, the upper surface of the grip part 2b of the plug body 2 and the inside surface of the head plate 3a of the cover member 3 face each other in parallel relation and with a gap therebetween. However, such a gap may not be provided. Specifically, as in a modification shown in FIG. 1(c), the upper surface of the plug body 2 may be engaged against the inside surface of the head plate 3a.

Furthermore, in FIG. 1(a) of this embodiment, the length H2 as a vertical dimension of the engagement portion 3d shown in FIG. 3(b) is set larger than the vertical dimension H1 of the inside wall 2e of the plug body 2 shown in FIG. 2(b). Therefore, the above-mentioned gap is created between the inside surface of the head plate 3a and the upper surface of the grip part 2b. And, as shown in FIG. 1(a), the distal end of the engagement portion 3d abuts against a portion of the plug body extending continuously from the lower end of the inside wall 2e.

The outside diameter of the engagement portion 3d is set approximately equal to the inside diameter of the recess defined by the inside wall 2e. Therefore, the outer peripheral surface of the engagement portion 3d, which is a cylindrically curved surface, faces and engages against the inside wall 2e.

However, the outer peripheral surface of the engagement portion 3d may face the inside wall 2e with a gap therebetween, as in a second embodiment to be described hereinafter and shown in FIG. 4. Preferably, it is desired that, as in the embodiment shown in FIG. 1, the outer peripheral surface of the engagement portion 3d be engaged against the inside wall 2e. In this case, even when upon removal an external force is applied obliquely upward to the cover member 3 while the cover member 3 is twisted relative to the bodily fluid collection tube, the force is immediately applied through the engagement portion to the inside wall 2e of the plug body 2. Thus, upon the removal to be described hereinafter, the plug body 2 and the cover member 3 can be unitarily and easily removed.

The plug 1 of this embodiment, as shown in FIG. 1(b), is attached to the opening 4a of the tubular container 4 to seal it. In use, for example, blood or the like is collected into the tubular container 4 using a vacuum blood collection needle. Next, to conduct a blood test or the like, the plug 1 is removed from the tubular container. In this removal, a portion of the skirt 3b of the cover member 3 is grasped with fingers and an external force is applied obliquely upward to the cover member 3 while the cover member 3 is twisted relative to the bodily fluid collection tube. Thus, the cover member 3 is removed together with the plug body 2 from the tubular container 4. In this case, even if the head plate 3a of the cover member 3 is urged to incline with respect to the upper surface of the plug body 2, the engagement portion 3d comes into close contact with the inside wall 2e to prevent the head plate 3a from moving away from the upper surface of the plug body 2. In other words, the engagement portion 3d is engaged to the inside wall 2e to avoid separation of the cover member 3 from the plug body 2. The plug body 2 can be thus easily removed together with the cover member 3 from the tubular container.

In addition, since, as described previously, the plug 1 is composed of two members: the plug body 2 and the cover member 3, it is prevented from increase in number of elements. Furthermore, the cover member 3 has a relatively simple structure in which the head plate 3a is provided with the engagement portion 3d. Therefore, the cover member 3 can be easily molded and easily fitted to the plug body 2. As a result, the cost can be reduced to increase the productivity.

Figure 4:
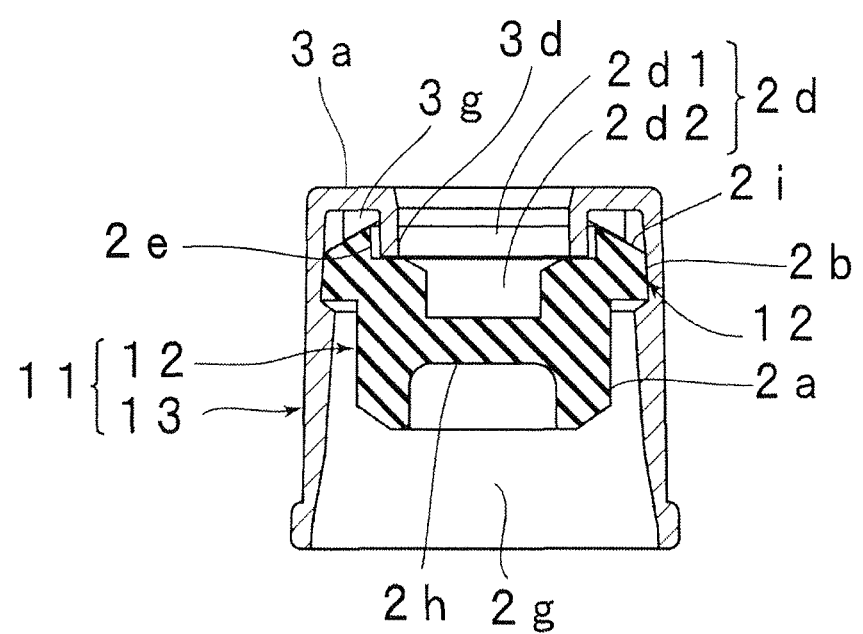
FIG. 4 is a front cross-sectional view for illustrating a plug according to a second embodiment of the present invention.

FIG. 4 is a front cross-sectional view showing a plug 11 according to a second embodiment of the present invention. A cover member 13 is fitted on a plug body 12. The plug 11 has substantially the same configuration as the plug 1 of the first embodiment except that the plug body 12 has an inclined surface 2i formed on the upper surface of the grip part 2b and that the cover member 13 includes ribs 3g provided on the inside surface of the head plate 3a. Therefore, like parts bear the same references and further explanation thereof will be accordingly omitted.

Figure 5:
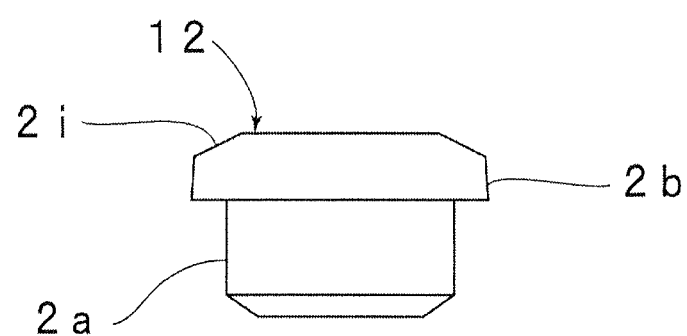
FIGS. 5(*a*) and 5(*b*) are a front view and a front cross-sectional view of a plug body used in the second embodiment.
Figure 5:
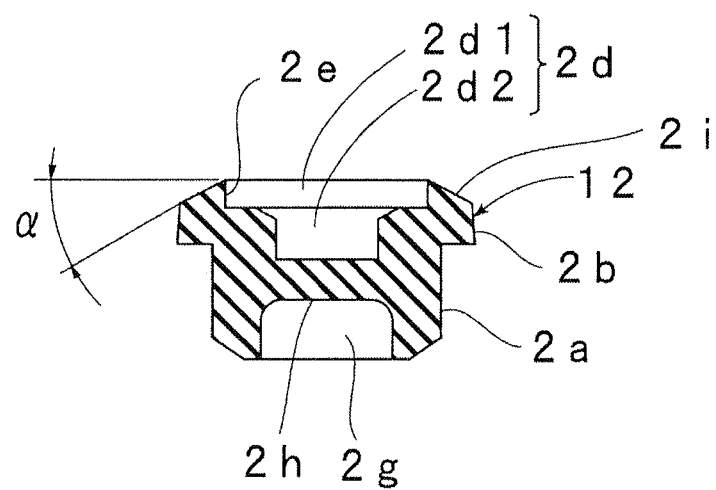

As shown in FIGS. 5(a) and 5(b), the height of the upper surface of the grip part 2b gradually decreases radially outward from the outer peripheral edge of the recess 2d provided in the upper surface of the plug body 2, so that an annular inclined surface 2i is formed on the upper surface of the grip part 2b.

Thus, as shown in FIG. 4, a space is created between the inclined surface 2i and the inside surface of the head plate 3a of the cover member 13. To prevent backlash due to this space, a plurality of ribs 3g are formed on the inside surface of the head plate 3a of the cover member 13.

Figure 6:
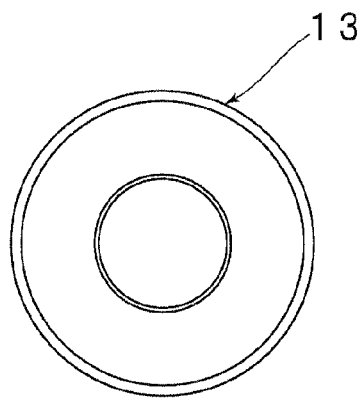
FIG. 6(*a*) is a plan view of a cover member used in the plug of the second embodiment of the present invention, FIG. 6(*b*) is a front cross-sectional view thereof, and FIG. 6(*c*) is a bottom view thereof.
Figure 6:
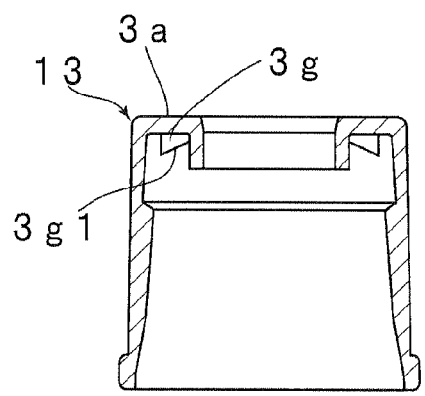
Figure 6:
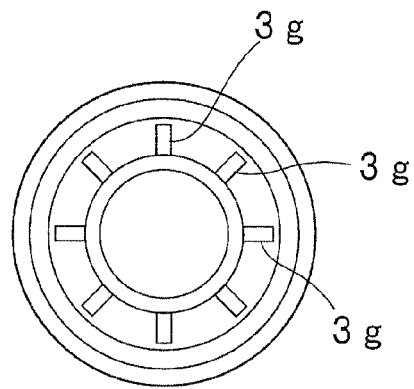

As shown in FIGS. 6(a) to 6(c), the cover member 13 includes the head plate 3a and the plurality of ribs 3g to be located in the space are formed on the inside surface of the head plate 3a. In this embodiment, the plurality of ribs 3g extend in the radial direction of the head plate 3a. Furthermore, the under surfaces of the ribs 3g are formed in inclined surfaces 3g1 gradually lowering from radially inner portion toward outer portion of the head plate 3a. These inclined surfaces 3g1 have a gradient equal to that of the inclined surface 2i of the plug body 2. And, when the cover member 13 is fitted on and locked to the plug body 12, the inclined surfaces 3g1 at the under surfaces of the ribs 3g engage against the inclined surface 2i of the plug body 2. Thus, with the plug body 12 locked to the cover member 13, the position of the plug body 12 can be stably retained. In this manner, if the plug body 2 has an inclined surface 2i, it is preferred that the above ribs 3g be provided integrally on the inside surface of the head plate 3a of the cover member 3.

As shown in FIG. 6(c), the plurality of ribs 3g are distributed at regular intervals in the circumferential direction of the head plate 3a. No particular limitation is placed on the number of the plurality of ribs 3g and any plurality of ribs 3g may be provided. Alternatively, a single rib may be provided the whole of which continues in an integral, thick-walled form.

However, preferably, it is desired to provide a plurality of ribs 3g, which can stabilize a state that the plug body 12 is fitted to the cover member 13.

Furthermore, the provision of a plurality of ribs 3g are preferably such that the angles formed by connecting the center of the head plate 3a and the ribs become equal to one another. Thus, variations of the position of the plug body 12 can be reduced.

Also when it is attempted to remove the plug 11 of this embodiment from the state where it is attached to the tubular container by applying an external force to the skirt 3b of the cover member 13, the engagement portion 3d engages against the inside wall 2e. Therefore, the plug body 12 can be easily and reliably removed together with the cover member 13 from the tubular container.

Next, a description will be given of specific experimental examples.

Example 1

The plug 1 shown in FIG. 1(a) was prepared. The plug body 2 used was one made of butyl rubber. The dimensions of the plug body 2 are as follows.

The outside diameter of the press-fit part 2a: 11 mm

The outside diameter of the grip part 2b: 15 mm
The thickness of the grip part 2b: 3 mm
The volume of the grip part 2b was 0.40 cm³. The opening diameter of the recess 2d, i.e., the diameter of a portion thereof surrounded by the inside wall 2e, was 10 mm.

A molded article made of a polyethylene-based synthetic resin was prepared as the cover member 3. In the cover member 3, the outside diameter of the engagement portion 3d in the head plate 3a was 9 mm. The dimension H2 from the inside surface of the head plate 3a to the lower end of the engagement portion 3d was 2 mm. Furthermore, the dimension H1 of the inside wall 2e of the plug body 2 in the height direction was 1.3 mm.

Example 2

In the plug body 12, the angle α of inclination of the inclined surface 2i shown in FIG. 5(b) was 26 degrees, the outside diameter of the press-fit part 2a was 11 mm, and the maximum outside diameter of the grip part 2b was 15 mm. Furthermore, the dimension H1 of the inside wall 2e in the height direction was 1.3 mm like Example 1.

The outside diameter of the head plate 3a of the cover member 13 was 16 mm and the length from the inside surface of the head plate 3a to the lower end of the engagement portion 3d was 2 mm.

The opening diameter of the recess 2d, i.e., the diameter of a portion thereof surrounded by the inside wall 2e, was 10 mm. The volume of the grip part 2b was 0.36 cm³.

Comparative Example 1

Figure 7:
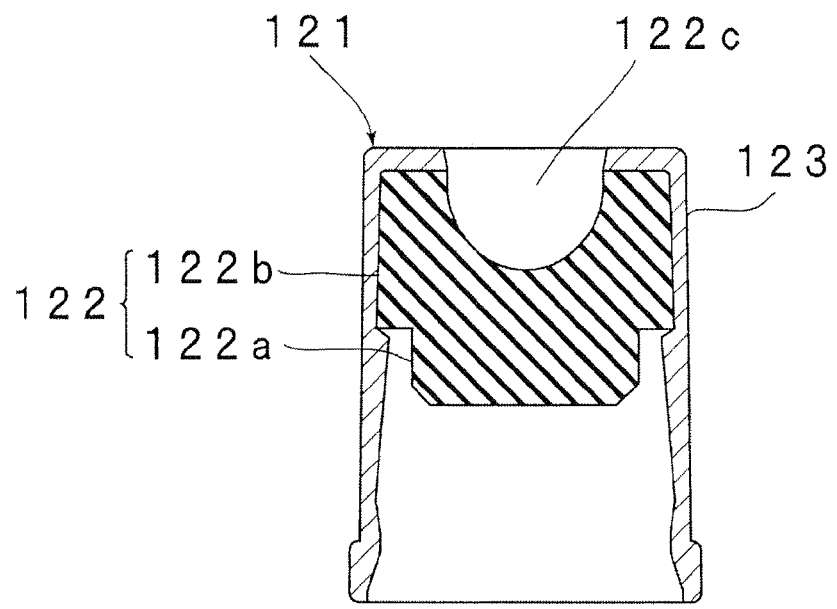
FIG. 7 is a front cross-sectional view showing a plug of a first comparative example.

The plug 121 shown in FIG. 7 was prepared as Comparative Example 1. In Comparative Example 1, the plug body 122 used was one including a press-fit part 122a with a cylindrical outside diameter of 11 mm and a grip part 122b with a cylindrical outside diameter of 15 mm. The upper surface of the plug body 122 had a recess 122c formed therein.

Figure 9:
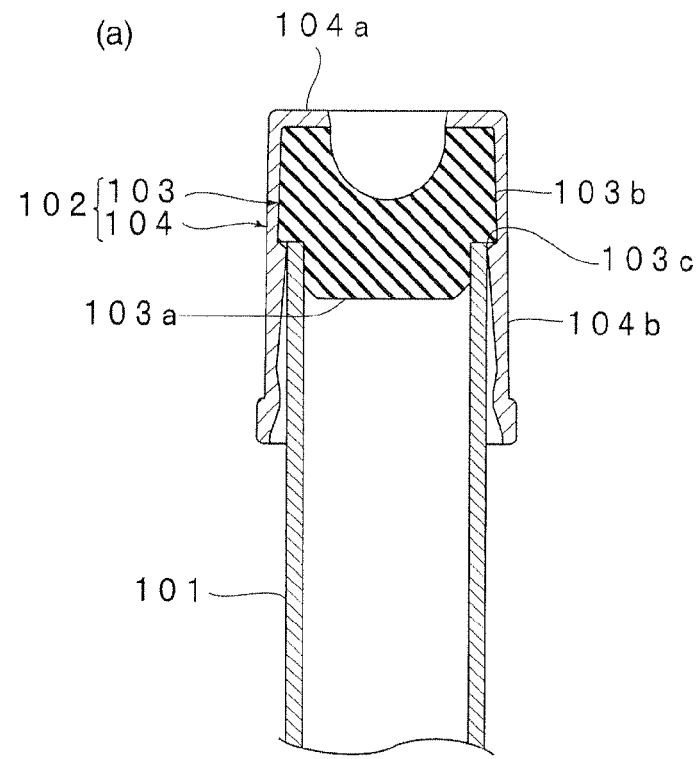
FIG. 9(a) is a partly cutaway front cross-sectional view showing a state that a conventional plug is attached to a tubular container and FIG. 9(b) is a front cross-sectional view for illustrating a problem of the conventional plug.
Figure 9:
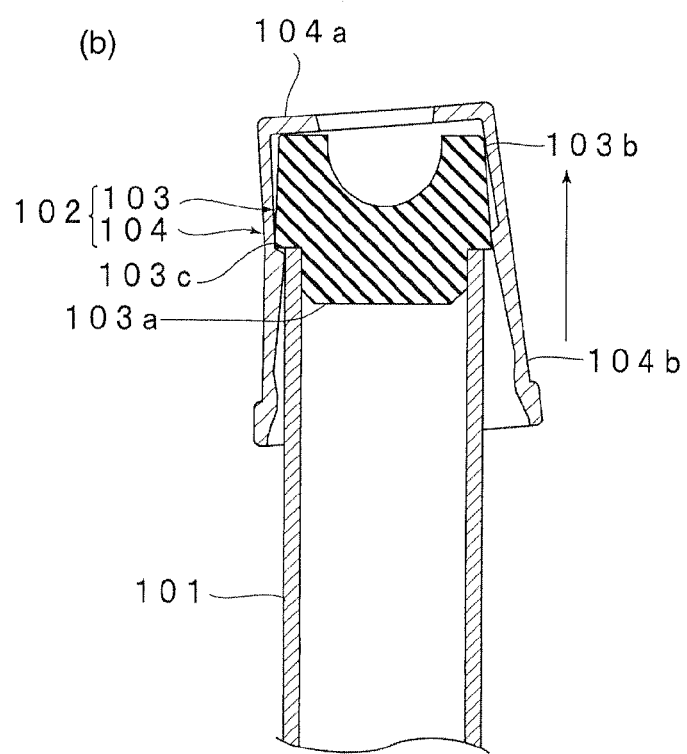
Figure 10:
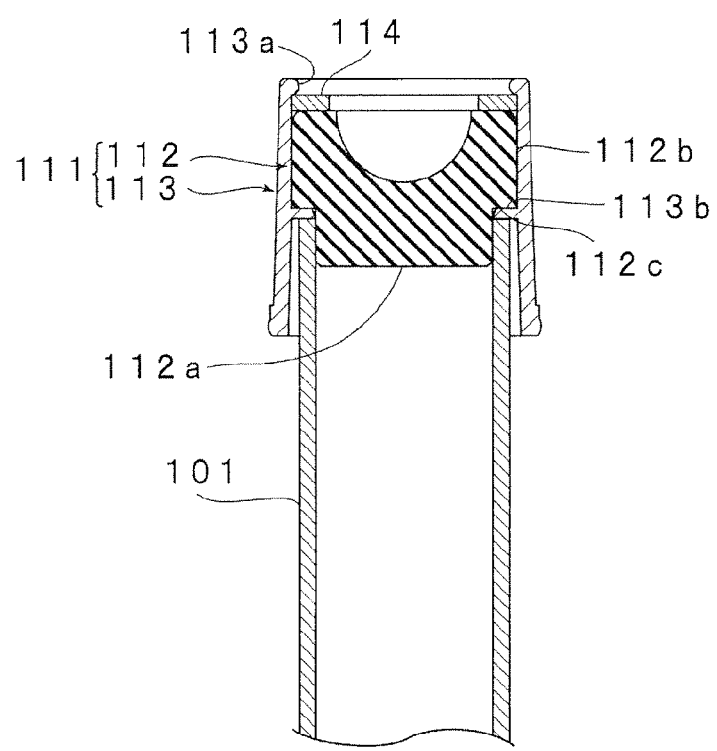
FIG. 10 is a partly cutaway front cross-sectional view for illustrating a state that another example of a conventional plug is attached to a tubular container.

On the other hand, the cover member 123 used was one having the same configuration as the cover member 104 shown in FIG. 9(a). In this case, the volume of the grip part was 1.10 cm³.

Comparative Example 2

Figure 8:
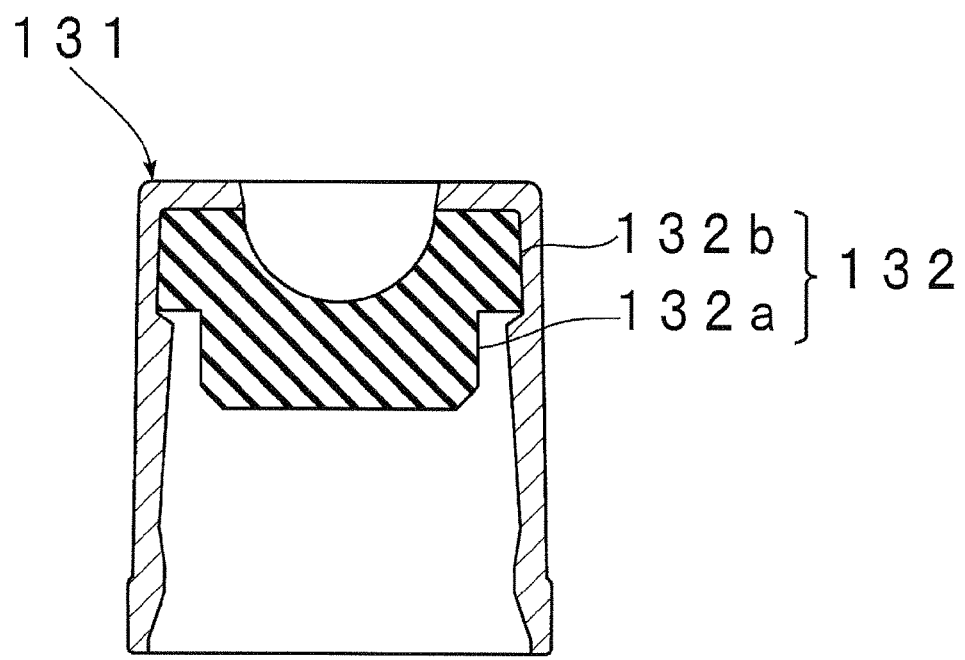
FIG. 8 is a front cross-sectional view showing a plug of a second comparative example.

The plug 131 shown in FIG. 8 was prepared as Comparative Example 2. The plug 131 of Comparative Example 2 had the same configuration as the plug 121 of Comparative Example 1. However, the volume of the grip part was 0.60 cm³.

Evaluation of Examples and Comparative Examples

Each plug was attached to a 7-mL volume, closed-bottomed, tubular container the upper end opening of which had an opening diameter of 10.7 mm. Thereafter, it was attempted to remove the cover member together with the plug body from the tubular container by grasping the skirt of the cover member with the hand, applying a force obliquely upward to the cover member while twisting it relative to the bodily fluid collection tube, and thus pushing up the cover member 3. For ten tubular containers, the above plug removal was attempted. Table 1 below shows the number of tubular containers for which the cover member was disengaged from the plug body and only the cover member was removed from the tubular container, resulting in failure to remove the plug body together with the cover member.

Table 1 also shows the volumes of the grip parts of the plug bodies.

TABLE 1

| | Number of Containers for which Cover Member was Disengaged from Plug Body | Grip Part Volume (cm³) |
| --- | --- | --- |
| Ex. 1 | 0 | 0.40 |
| Ex. 2 | 0 | 0.36 |
| Comp. Ex. 1 | 1 | 1.10 |
| Comp. Ex. 2 | 10 | 0.60 |

As is evident from Table 1, in Comparative Example 1 and Comparative Example 2, there were cases where only the cover member was detached. Particularly in Comparative Example 2 in which the grip part of the plug body was decreased in volume from 1.10 cm³ to 0.60 cm³, size reduction could be achieved but, in all the cases of the ten tubular containers, only the cover member was detached.

In contrast, in Examples 1 and 2, the grip parts of the plug bodies were decreased in volume to 0.40 cm³ and 0.36 cm³, respectively, but nevertheless the plug bodies could be reliably removed together with the cover members.

Therefore, in Examples 1 and 2, the volume of the grip part of the plug body can be decreased to approximately 40% of that in Comparative Example 1. Hence, it can be seen that the amount of waste after the collection of bodily fluid can be reduced to reduce environmental burden.

REFERENCE SIGNS LIST

1 . . . plug
2 . . . plug body
2a . . . press-fit part
2b . . . grip part
2c . . . annular shoulder
2d . . . recess
2e . . . inside wall
2f . . . annular inclined surface
2g . . . recess
2h . . . thin-walled portion
2i . . . inclined surface
3 . . . cover member
3a . . . head plate
3b . . . skirt
3c . . . opening
3d . . . engagement portion
3e . . . annular shoulder
3g . . . rib
3g1 . . . inclined surface
4 . . . tubular container
4a . . . opening
11 . . . plug
12 . . . plug body
13 . . . cover member
101 . . . bodily fluid collection tube
102 . . . plug
103 . . . plug body
103a . . . press-fit part
103b . . . grip part
103c . . . annular shoulder
104 . . . cover member
104a . . . head plate
104b . . . skirt 111 . . . plug
112 . . . plug body
112a . . . press-fit part
112b . . . grip part
112c . . . shoulder
113 . . . cover member
113a . . . annular extension
113b . . . annular engagement ledge
114 . . . ring
121 . . . plug
122 . . . plug body
122a . . . press-fit part
122b . . . grip part
122c . . . recess
123 . . . cover member
131 . . . plug
132 . . . plug body
132a . . . press-fit part
132b . . . grip part

The invention claimed is:

1. A plug for closing an open end of an open-ended tubular container, comprising:
a plug body which includes
a press-fit part to be press-fitted into the open end of the tubular container, and
a grip part continuous with the top of the press-fit part and having a larger diameter than the press-fit part,
wherein an upper surface of the grip part has a recess formed therein and surrounded by an inside wall extending downward; and
a cover member including a head plate and a skirt extending downward from a peripheral edge of the head plate, the cover member fitted on the plug body so that a lower surface of the head plate and the upper surface of the grip part of the plug body face each other,
wherein an engagement portion provided at the head plate of the cover member and engaged to the inside wall surrounding the recess of the entire plug is extended from the head plate of the cover member to the interior of the recess to face a surface of the inside wall surrounding the recess of the plug body, and
wherein at least a portion of an inside surface of the head plate of the cover member is engaged against the upper surface of the grip part of the plug body, and
wherein an outer peripheral edge of the grip part of the plug body is located below an outer peripheral edge of the recess in the grip part to thus create a space between the head plate of the cover member and the upper surface of the plug body,
the head plate of the cover member being provided at a portion thereof facing the space with a rib extending downward from the head plate into the space, but not completely filling the space, and abutting the upper surface of the grip part of the plug body.

2. The plug according to claim 1, wherein the engagement portion is engaged against the inside wall surrounding the recess of the plug body.

3. The plug according to claim 1, wherein the inside wall surrounding the recess of the plug body is an annular inside wall and the engagement portion includes a curved surface portion having a shape fitting the annular inside wall.

4. The plug according to claim 3, wherein the engagement portion has a cylindrical shape.

5. The plug according to claim 1, wherein the upper surface of the grip part of the plug body is an inclined surface gradually lowering from the outer peripheral edge of the recess toward the outer peripheral edge of the grip part and the rib is provided to engage against the inclined surface,
wherein the grip part includes an outer side surface extending downward from the outer peripheral edge of the grip part, and
wherein the rib is provided on the inside surface of the head plate of the cover member.

6. The plug according to claim 2, wherein the inside wall surrounding the recess of the plug body is an annular inside wall and the engagement portion includes a curved surface portion having a shape fitting the annular inside wall.

7. The plug according to claim 6, wherein the engagement portion has a cylindrical shape.

8. The plug according to claim 1, wherein the upper surface of the grip part of the plug body is an inclined surface gradually lowering from the outer peripheral edge of the recess toward the outer peripheral edge of the grip part and the rib is provided to engage against the inclined surface,
wherein the grip part includes an outer side surface extending downward from the outer peripheral edge of the grip part, and
wherein the rib is provided on the inside surface of the head plate of the cover member.

* * * * *